United States Patent
Iwai et al.

(10) Patent No.: US 8,305,584 B2
(45) Date of Patent: Nov. 6, 2012

(54) MEASUREMENT INSTRUMENT OF OPTICAL CHARACTERISTICS FOR SAMPLE FLOWING IN PASSAGE

(75) Inventors: Hidenao Iwai, Hamamatsu (JP); Toyohiko Yamauchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 186 days.

(21) Appl. No.: 12/671,051

(22) PCT Filed: Jun. 3, 2008

(86) PCT No.: PCT/JP2008/060198
§ 371 (c)(1),
(2), (4) Date: Mar. 2, 2010

(87) PCT Pub. No.: WO2009/016887
PCT Pub. Date: Feb. 5, 2009

(65) Prior Publication Data
US 2010/0195110 A1 Aug. 5, 2010

(30) Foreign Application Priority Data

Jul. 31, 2007 (JP) .............................. P2007-199595

(51) Int. Cl.
*G01B 9/02* (2006.01)
(52) U.S. Cl. ..................................................... 356/477
(58) Field of Classification Search .................. 356/477, 356/479; 250/227, 19, 227.27
See application file for complete search history.

(56) References Cited

U.S. PATENT DOCUMENTS 5,459,570 A * 10/1995 Swanson et al. .............. 356/479
5,710,630 A * 1/1998 Essenpreis et al. ........... 356/479
6,590,664 B1 * 7/2003 Dogariu et al. ................ 356/479
7,102,756 B2 * 9/2006 Izatt et al. ...................... 356/479
7,426,038 B2 * 9/2008 Ogawa ........................... 356/484

(Continued)

FOREIGN PATENT DOCUMENTS

JP 2-0140639 5/1990

(Continued)

OTHER PUBLICATIONS

Erik B. van Munster, "Interferometry in Flow to Sort Unstained X- and Y-Chromosome-Bearing Bull Spermatozoa," Cytometry, 2002, vol. 47, pp. 192-199.

*Primary Examiner* — Michael A Lyons
(74) *Attorney, Agent, or Firm* — Drinker Biddle & Reath LLP

(57) ABSTRACT

An optical property measurement apparatus includes a light source unit, a first optical coupler, a second optical coupler, a lens, a lens, a phase modulation unit, a drive unit, an optical path length difference adjustment unit, a control unit, a light receiving unit, a synchronization detection unit, and a measurement unit. The phase modulation unit carries out phase modulation with a frequency f. The synchronization detection unit outputs a first signal having a value corresponding to a magnitude of a component of the frequency f included in an electrical signal output from the light receiving unit, and also outputs a second signal having a value corresponding to a magnitude of a component of the frequency 2f included in the electrical signal. The control unit controls the optical path length difference adjusted by the optical path length difference adjustment unit to be a predetermined value based on the first signal or the second signal output from the synchronization detection unit.

2 Claims, 14 Drawing Sheets

U.S. PATENT DOCUMENTS

2005/0105097 A1   5/2005   Fang-Yen et al.
2005/0122528 A1   6/2005   Iwai et al.

FOREIGN PATENT DOCUMENTS

| JP | 7-119613 | 12/1995 |
| --- | --- | --- |
| JP | H9-512722 | 12/1997 |
| JP | 10-232204 | 9/1998 |
| JP | 10-267610 | 10/1998 |
| JP | 11-108763 | 4/1999 |
| JP | 2001-4538 | 1/2001 |
| JP | 2003-307487 | 10/2003 |
| JP | 2005-121600 | 5/2005 |
| JP | 2007-155452 | 6/2007 |
| WO | 2005/001445 | 1/2005 |
| WO | 2005/015149 | 2/2005 |

\* cited by examiner (a)

(b)

(a)

(b)

MEASUREMENT INSTRUMENT OF OPTICAL CHARACTERISTICS FOR SAMPLE FLOWING IN PASSAGE

TECHNICAL FIELD

The present invention relates to an optical property measurement apparatus for measuring an optical property of a sample flowing in a flow passage by use of optical interference.

BACKGROUND ART

An optical property measurement apparatus using optical interference has been disclosed in, for example, Patent Documents 1 and 2. An optical property measurement apparatus using a Mach-Zehnder interferometer can measure an optical property of a sample in a flow passage. That is, this type of optical property measurement apparatus causes one of branched light which is branched into two by a first optical coupler to cross a flow passage and causes this branched light and the other branched light to interfere by a second optical coupler to detect intensity of the interfering light, so that the optical property of a sample in the flow passage can be measured.

The optical properties of the sample specifically mean an optical thickness, a refractive index, absorption, and the like. Such data allows an operator to determine size (volume) or dry weight of a sample such as a cell. A phase difference is measured by a measurement unit. Here, it is assumed that change amount of a phase difference $\phi$ by passing through a sample is $\Delta\phi_S$. In a case where, for example, it is desired to measure an optical thickness of the sample, the optical thickness of the cell can be calculated by "$\Delta\phi_S (\lambda/2\pi)$". If the refractive index of the sample can be obtained, it is also possible to calculate the particle diameter of the sample. The optical thickness is proportional to the volume in a case where distribution of the refractive index in the sample is uniform, while it is proportional to the dry weight of the sample in a case where the distribution is not uniform (refer to Non-Patent Document 1). Moreover, for the refractive index of the sample, an average refractive index difference (refractive difference between a solvent and the sample) can be calculated by a formula of "$\Delta\phi_S (\lambda/2\pi)/D$." Here, D indicates the diameter of the particle. Further, if sum of squares of signals Asin $\phi$ and Acos $\phi$ which are input into the measurement unit are obtained, an amplitude A is obtained and absorption of the sample can be measured by a degree of attenuation of amplitude intensity. $\lambda$ indicates wavelength of light.

Patent Document 1: Japanese Patent Publication No. H7-119613
Patent Document 2: US Patent Application Publication No. 2005/0105097
Non-Patent Document 1: E. B. van Munster, Cytometry, Vol. 47, pp. 192-199 (2002).

DISCLOSURE OF THE INVENTION

Problems to be Solved by the Invention

In the above-described optical property measurement apparatus, there is a case where part or all of each of two branched light paths between the first optical coupler and the second optical coupler includes an optical fiber. In this case, there may be a case where the optical fiber is extended or contracted due to change in environment such as temperature and a difference in the optical path lengths of the two branched light paths varies to change the intensity of the interfering light. The change in intensity of the interfering light becomes a noise in measurement.

Linear expansion coefficient of a glass fiber is, in general, $100 \times 10^{-7}$/K, and variation width and frequency of extension and contraction of the fiber depend on the usage environment thereof. For example, if a length of the optical fiber is 2 m, and a temperature variation is 1° C., extension and contraction of the optical fiber is approximately 20 μm and frequency of variation of extension and contraction of the optical fiber (i.e., noise frequency) is approximately 0.2 Hz. If frequency of signal light generated by the measurement target is sufficiently larger than the noise frequency, for example, 10 kHz or more, noise component can be eliminated by a method of frequency discrimination and the signal light can be selectively extracted.

Moreover, there may be a case where a difference in the optical path lengths of the two branched light paths varies due to a change in environment such as temperature and measurement sensitivity is deteriorated. That is, if the optical path length difference is a predetermined value, the measurement sensitivity is maximized, however, if the optical path length difference is out of the range of the predetermined value, measurement sensitivity is deteriorated and SN ratio is deteriorated. Therefore, a mechanism for controlling the difference in the optical path lengths to be constant is required to maintain the measurement sensitivity to be constant.

In a case where an optical property of a sample in a flow passage is measured, because each of the sample particles is moving one by one, signal light is generated when a sample particle is crossing the branched light, while signal light is not generated when a sample particle is not crossing the branched light. According to a general technique such as used in a flow cytometer, light does not reach a photodetector when a sample is not passing through. Such a configuration improves measurement sensitivity because, in a case where light intensity is measured, a signal component is detected only when a sample passes through. Even when a sample particle is not crossing the branched light, the optical path length difference varies and measurement sensitivity varies, and therefore, in a case where phase difference is measured, it is required to control the difference in the optical path lengths to be constant.

However, according to the general technique, since the light does not reach the photodetector when a sample particle is not crossing the branched light, it is not possible to always control the optical path length difference to be constant. Therefore, even when each of the sample particles is crossing the branched light, the difference in the optical path lengths is out of the range of the predetermined value and measurement sensitivity is not constant.

The present invention has been made to solve the above-described problem, and it is therefore an object of the invention to provide an optical property measurement apparatus which can measure an optical property of a sample with a constant sensitivity even in a case where each of the sample particles are moving in a flow passage one by one.

Means for Solving the Problems

An optical property measurement apparatus according to a first aspect of the present invention is an optical property measurement apparatus for measuring an optical property of a sample in a flow passage using optical interference, and includes (1) a light source unit for emitting light, (2) a first optical coupler for branching the light emitted from the light source unit into two components and outputting the light components as first branched light and second branched light, (3) a second optical coupler for inputting the first branched light output from the first optical coupler and passed through a first branched light path, inputting the second branched light output from the first optical coupler and passed through a second branched light path and a flow passage on the second branched light path, and causing the first branched light and the second branched light thus input to interfere with each other to output interfering light, (4) a phase modulation unit provided on the first branched light path or the second branched light path between the first optical coupler and the second optical coupler for carrying out phase modulation of the light, which is propagated on the light path, with a frequency f, and (5) an optical path length difference adjustment unit for adjusting a difference in the optical path lengths of the first branched light path and the second branched light path between the first optical coupler and the second optical coupler.

The optical property measurement apparatus according to the first aspect of the present invention further includes (6) a light receiving unit for receiving the interfering light output from the second optical coupler and outputting an electrical signal having a value corresponding to the received light intensity, (7) a synchronization detection unit for inputting the electrical signal output from the light receiving unit, outputting a first signal having a value which corresponds to a magnitude of a component of the frequency f included in the electrical signal, and outputting a second signal having a value which corresponds to a magnitude of a component of a frequency 2f included in the electrical signal, (8) a control unit for controlling the optical path length difference adjusted by the optical path length difference adjustment unit to be a predetermined value based on the first signal or the second signal output from the synchronization detection unit, and (9) a measurement unit for measuring an optical property of a sample in the flow passage based on the first signal and the second signal output from the synchronization detection unit.

In the optical property measurement apparatus according to the first aspect of the present invention, light output from the light source unit is branched into two by the first optical coupler and is output as the first branched light and the second branched light. The first branched light which is output from the first optical coupler and passed through the first branched light path is input into the second optical coupler. The second branched light which is output from the first optical coupler and passed through the second branched light path and the flow passage provided on the second branched light path is also input into the second optical coupler. The first branched light and the second branched light thus input in the second optical coupler are caused to interfere and the interfering light is output from the second optical coupler. The first optical coupler, the second optical coupler, the first branched light path, and the second branched light path configure a Mach-Zehnder interferometer. The phase modulation unit provided on either the first branched light path or the second branched light path between the first optical coupler and the second optical coupler carries out phase modulation of the light, which is propagated on the light path, with the frequency f. The difference in the optical path lengths of the first branched light path and the second branched light path between the first optical coupler and the second optical coupler is adjusted by the optical path length difference adjustment unit.

The interfering light output from the second optical coupler is received by the light receiving unit and an electrical signal having a value corresponding to the intensity of the received light is output from the light receiving unit. The electrical signal output from the light receiving unit is input into the synchronization detection unit, and the first signal having a value which corresponds to the magnitude of the component of the frequency f included in the electrical signal is output from the synchronization detection unit, and at the same time, the second signal having a value which corresponds to the magnitude of the component of the frequency 2f included in the electrical signal is output from the synchronization detection unit. Then, on the basis of the first signal or the second signal output from the synchronization detection unit, the difference in the optical path lengths which is adjusted by the optical path length difference adjustment unit is controlled to be a predetermined value by the control unit. Moreover, on the basis of the first signal and the second signal output from the synchronization detection unit, an optical property of the sample in the flow passage is measured by the measurement unit.

Further, an optical property measurement apparatus according to a second aspect of the present invention is an optical property measurement apparatus for measuring an optical property of a sample in a flow passage by use of optical interference, and includes (1) a light source unit for emitting light, (2) a first optical coupler for branching the light emitted from the light source unit into two components and outputting the light components as first branched light and second branched light, (3) a second optical coupler for inputting the first branched light output from the first optical coupler and passed through a first branched light path, inputting the second branched light output from the first optical coupler and passed through a second branched light path and a flow passage on the second branched light path, and causing the first branched light and the second branched light thus input to interfere with each other to output interfering light, (4) a phase modulation unit provided on the first branched light path or the second branched light path between the first optical coupler and the second optical coupler for carrying out phase modulation of the light, which is propagated on the light path, with a frequency f, and (5) an optical path length difference adjustment unit for adjusting a difference in the optical path lengths of the first branched light path and the second branched light path between the first optical coupler and the second optical coupler.

The optical property measurement apparatus according to the second aspect of the present invention further includes (6a) a first light receiving unit for selectively receiving zero-order light in the interfering light output from the second optical coupler and outputting a first electrical signal having a value corresponding to the received light intensity, (6b) a second light receiving unit for selectively receiving high-order light in the interfering light output from the second optical coupler and outputting a second electrical signal having a value corresponding to the received light intensity, (7a) a first synchronization detection unit for inputting the first electrical signal output from the first light receiving unit, and outputting a first signal having a value which corresponds to a magnitude of a component of the frequency f included in the first electrical signal, or a second signal having a value which corresponds to a magnitude of a component of a frequency 2f included in the first electrical signal, (7b) a second synchronization detection unit for inputting the second electrical signal output from the second light receiving unit, outputting a third signal having a value which corresponds to a magnitude of a component of the frequency f included in the second electrical signal, and outputting a fourth signal having a value which corresponds to a magnitude of a component of the frequency 2f included in the second electrical signal, (8) a control unit for controlling the optical path length difference adjusted by the optical path length difference adjustment unit to be a predetermined value based on the first signal or the second signal output from the first synchronization detection unit, and (9) a measurement unit for measuring an optical property of a sample in the flow passage based on the third signal and the fourth signal output from the second synchronization detection unit.

In the optical property measurement apparatus according to the second aspect of the present invention, light output from the light source unit is branched into two by the first optical coupler and is output as the first branched light and the second branched light. The first branched light which is output from the first optical coupler and passed through the first branched light path is input into the second optical coupler. The second branched light which is output from the first optical coupler and passed through the second branched light path and the flow passage provided on the second branched light path is also input into the second optical coupler. The first branched light and the second branched light thus input in the second optical coupler are caused to interfere and the interfering light is output from the second optical coupler. The first optical coupler, the second optical coupler, the first branched light path, and the second branched light path configure a Mach-Zehnder interferometer. The phase modulation unit provided on either the first branched light path or the second branched light path between the first optical coupler and the second optical coupler carries out phase modulation of the light, which is propagated on the light path, with the frequency f. The difference in the optical path lengths of the first branched light path and the second branched light path between the first optical coupler and the second optical coupler is adjusted by the optical path length difference adjustment unit.

The zero-order light of the interfering light output from the second optical coupler is selectively received by the first light receiving unit and a first electrical signal having a value corresponding to the intensity of the received light is output from the first light receiving unit. The high-order light of the interfering light output from the second optical coupler is selectively received by the second light receiving unit and a second electrical signal having a value corresponding to the intensity of the received light is output from the second light receiving unit. The first electrical signal output from the first light receiving unit is input into the first synchronization detection unit and the first signal having a value which corresponds to the magnitude of the component of the frequency f included in the first electrical signal or the second signal having a value which corresponds to the magnitude of the component of the frequency 2f included in the first electrical signal is output from the first synchronization detection unit. The second electrical signal output from the second light receiving unit is input into the second synchronization detection unit and the third signal having a value which corresponds to the magnitude of the component of the frequency f included in the second electrical signal is output from the second synchronization detection unit, and at the same time, the fourth signal having a value which corresponds to the magnitude of the component of the frequency 2f included in the second electrical signal is output from the second synchronization detection unit. Then, on the basis of the first signal or the second signal output from the first synchronization detection unit, the difference in the optical path lengths which is adjusted by the optical path length difference adjustment unit is controlled to be a predetermined value by the control unit. Moreover, on the basis of the third signal and the fourth signal output from the second synchronization detection unit, an optical property of the sample in the flow passage is measured by the measurement unit.

Here, a preferable target for measurement by the optical property measurement apparatus according to the present invention is the sample in a case where each of the sample particles moves in a flow passage one by one. The flow passage may be a flow cell or a capillary including a glass tube, or may be a blood vessel of a living body.

EFFECT OF THE INVENTION

According to the present invention, it is possible to measure the optical property of the sample with a constant sensitivity even in a case where each of the sample particles moves in a flow passage one by one.

Figure 1:
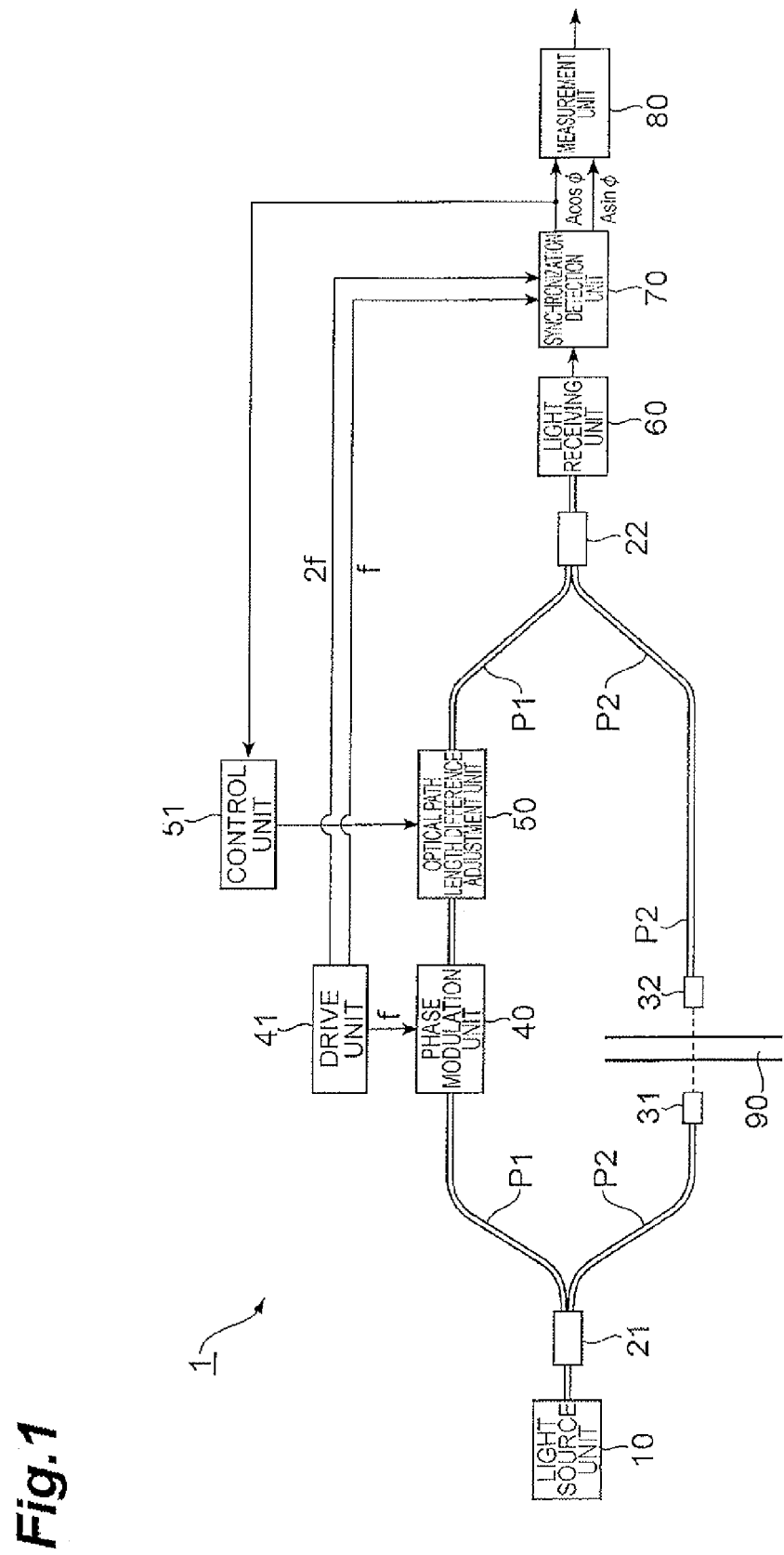
FIG. 1 is a view showing a configuration of an optical property measurement apparatus 1 according to a first embodiment.

DESCRIPTION OF THE SYMBOLS 1, 2—Optical property measurement apparatus, 10—Light source unit 10, 21, 22—Optical coupler, 31 to 32—Lens, 40—Phase modulation unit, 41—Drive unit, 50—Optical path length difference adjustment unit, 51—Control unit, 60 to 62—Light receiving unit, 70 to 72—Synchronization detection unit, 80—Measurement unit.

BEST MODES FOR CARRYING OUT THE INVENTION

Hereinafter, preferred embodiments for carrying out the present invention will be described in detail with reference to the accompanying drawings. Here, in the description of the drawings, the same reference numerals are given to the same components and redundant explanation thereof is omitted.

First Embodiment

First, a first embodiment of an optical property measurement apparatus according to the present invention will be explained. FIG. 1 is a view showing a configuration of an optical property measurement apparatus 1 according to the first embodiment. The optical property measurement apparatus 1 according to the first embodiment shown in the figure includes a light source unit 10, a first optical coupler 21, a second optical coupler 22, a lens 31, a lens 32, a phase modulation unit 40, a drive unit 41, an optical path length difference adjustment unit 50, a control unit 51, a light receiving unit 60, a synchronization detection unit 70, and a measurement unit 80.

The light source unit 10 emits coherent light and is preferably a laser light source, and more preferably, the light source unit is a semiconductor laser light source or a super luminescence diode.

The first optical coupler 21 branches the light emitted from the light source unit 10 into two and outputs the branched light components as first branched light and second branched light. The first optical coupler 21 outputs the first branched light to a first branched light path P1 and outputs the second branched light to a second branched light path P2. The second optical coupler 22 inputs the first branched light output from the first optical coupler 21 and passed through the first branched light path P1 and also inputs the second branched light output from the first optical coupler 21, passed through the second branched light path P2, and passed through a flow passage 90 on the second branched light path P2, and then, the second optical coupler causes the first branched light and the second branched light thus input to interfere with each other and outputs interfering light to the light receiving unit 60. Each of the first optical coupler 21 and the second optical coupler 22 may be a beam splitter or an optical fiber coupler. The first optical coupler 21, the second optical coupler 22, the first branched light path P1, and the second branched light path P2 configure a Mach-Zehnder interferometer.

The lens 31 and the lens 32 are provided on the second branched light path P2 between the first optical coupler 21 and the second optical coupler 22 in a manner that the lenses face each other with the flow passage 90 therebetween. The lens 31 collimates or converges the second branched light, which is output from the first optical coupler 21 and guided by an optical fiber to reach the lens, and output the light outside. The lens 32 inputs the second branched light output from the lens 31 and causes the second branched light to be guided toward the second optical coupler 22 by an optical fiber.

The phase modulation unit 40 and the optical path length difference adjustment unit 50 are respectively provided on the first branched light path P1 between the first optical coupler 21 and the second optical coupler 22. The phase modulation unit 40 is driven by a modulation signal of a frequency f output from the drive unit 41 and carries out phase modulation of the first branched light which is propagated on the first branched light path P1 with the frequency f sinusoidally. The phase modulation unit 40 uses, for example, a $LiNbO_3$ crystal, modulation speed thereof is 2.5 Gbit/s, drive voltage required to change the phase by $\pi$ is 5V or less, and the phase modulation unit carries out phase modulation on the first branched light to be sinusoidal by 5 MHz. As the drive unit 41, for example, a drive circuit is used.

The optical path length difference adjustment unit 50 is controlled by the control unit 51 and adjusts the optical path length of the first branched light path P1 to adjust the difference in the optical path lengths of the first branched light path P1 and the second branched light path P2 between the first optical coupler 21 and the second optical coupler 22. Various types of optical path length difference adjustment units 50 may be used, and for example, as described later using FIG. 2 to FIG. 8, one which enables to change the optical path length of an optical fiber by twisting the optical fiber around a cylindrical piezoelectric vibrator or one which enables to change an interval between two opposite mirrors by a piezoelectric element may be adopted. As the control unit 51, for example, a PID controller is used.

Here, it is preferable that each of a light path between the first optical coupler 21 and the phase modulation unit 40, a light path between the phase modulation unit 40 and the optical path length difference adjustment unit 50, a light path between the optical path length difference adjustment unit 50 and the second optical coupler 22, a light path between the first optical coupler 21 and the lens 31, a light path between the lens 32 and the second optical coupler 22 includes an optical fiber.

The light receiving unit 60 receives the interfering light output from the second optical coupler 22 and outputs an electrical signal having a value corresponding to the received light intensity to the synchronization detection unit 70. The light receiving unit 60 includes, for example, a photodiode. The synchronization detection unit 70 inputs the electrical signal output from the light receiving unit 60, and also inputs a modulation signal of a frequency f and a modulation signal of a frequency 2f from the drive unit 41. Then, the synchronization detection unit 70 outputs a first signal having a value corresponding to the magnitude of the component of the frequency f included in the electrical signal output from the light receiving unit 60, and also outputs a second signal having a value corresponding to the magnitude of the component of the frequency 2f included in the electrical signal. The synchronization detection unit 70 includes, for example, a lock-in amplifier.

The measurement unit 80 measures an optical property of a sample in the flow passage 90 on the basis of the first signal and the second signal output from the synchronization detection unit 70. Moreover, the control unit 51 controls the optical path length difference, which is adjusted by the optical path length difference adjustment unit 50, to be a predetermined value on the basis of the first signal or the second signal (or on the basis of values of both the first signal and the second signal) output from the synchronization detection unit 70. For example, the optical property measurement apparatus 1 shown in FIG. 1 or an optical property measurement apparatus 2 shown in FIG. 11 controls on the basis of only the second signal. Here, it is preferable that the control by the control unit 51 is carried out via a low-pass filter which transmits a variation frequency of the optical path length difference caused by change in environment such as temperature and blocks a frequency including a signal generated when a sample passes through.

Next, configuration examples of the optical path length difference adjustment unit 50 included in the optical property measurement apparatus 1 according to the first embodiment will be explained using FIG. 2 to FIG. 8.

Figure 2:
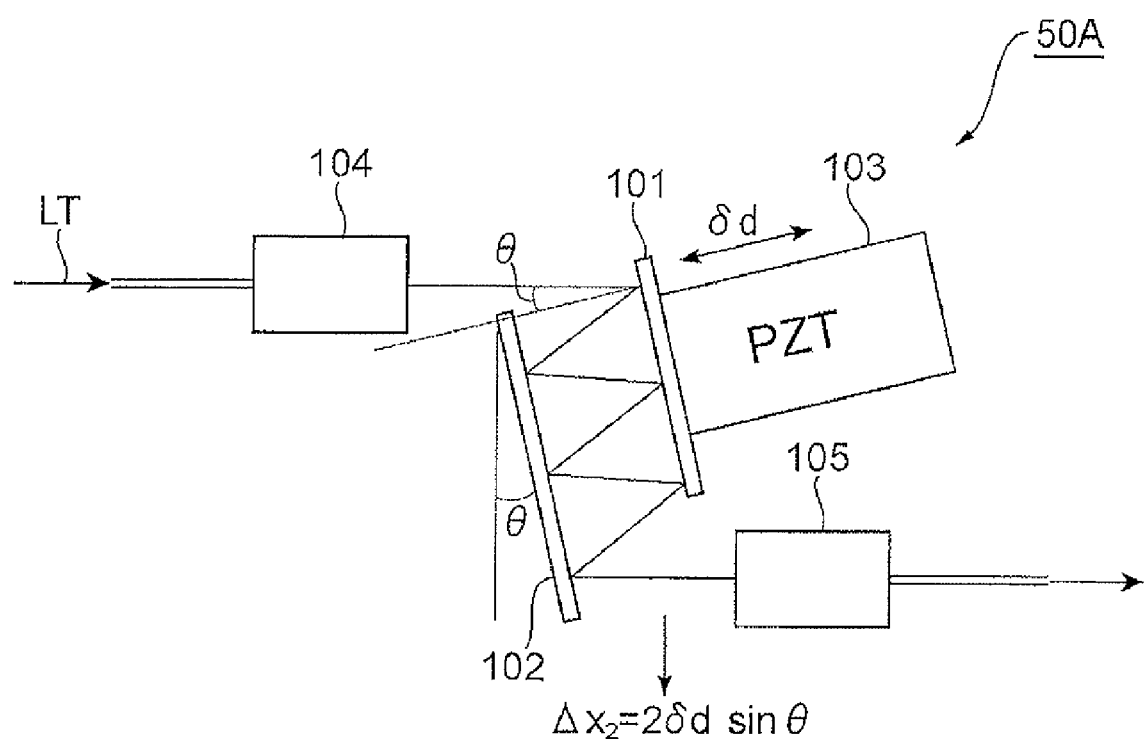
FIG. 2 is a view showing a configuration of an optical path length difference adjustment unit 50A as an example of an optical path length difference adjustment unit 50.

FIG. 2 is a view showing a configuration of an optical path length difference adjustment unit 50A as an example of the optical path length difference adjustment unit 50. The optical path length difference adjustment unit 50A shown in this figure includes a mirror 101, a mirror 102, a piezoelectric element 103, a collimator 104, and a collimator 105. The mirror 101 and mirror 102 are respectively provided so that flat reflection surfaces thereof face each other, and an interval between the two mirrors can be changed when the one mirror 101 is moved by the piezoelectric element 103 in a direction perpendicular to the reflection surface. The collimator 104 is provided on an output end of an optical fiber which guides light LT output from the phase modulation unit 40. The collimator 105 is provided on an input end of an optical fiber which guides the light to the second optical coupler 22.

The light collimated and output from the collimator 104 is reflected by the mirror 101 first and subsequently reflected by the mirror 101 and the mirror 102 in a repeated manner to be finally reflected by the mirror 102 and input into the collimator 105. The mirror 101 is moved by the piezoelectric element 103 in this optical path length difference adjustment unit 50A to change the interval between the mirror 101 and the mirror 102, so that the optical path length between the collimator 104 and the collimator 105 is changed.

For example, the interval between the mirror 101 and the mirror 102 is 10 mm, stroke of the piezoelectric element 103 is 6 μm, and repeated reflection by the mirror 101 and the mirror 102 is carried out 12 times (6 times for one mirror).

Figure 3:
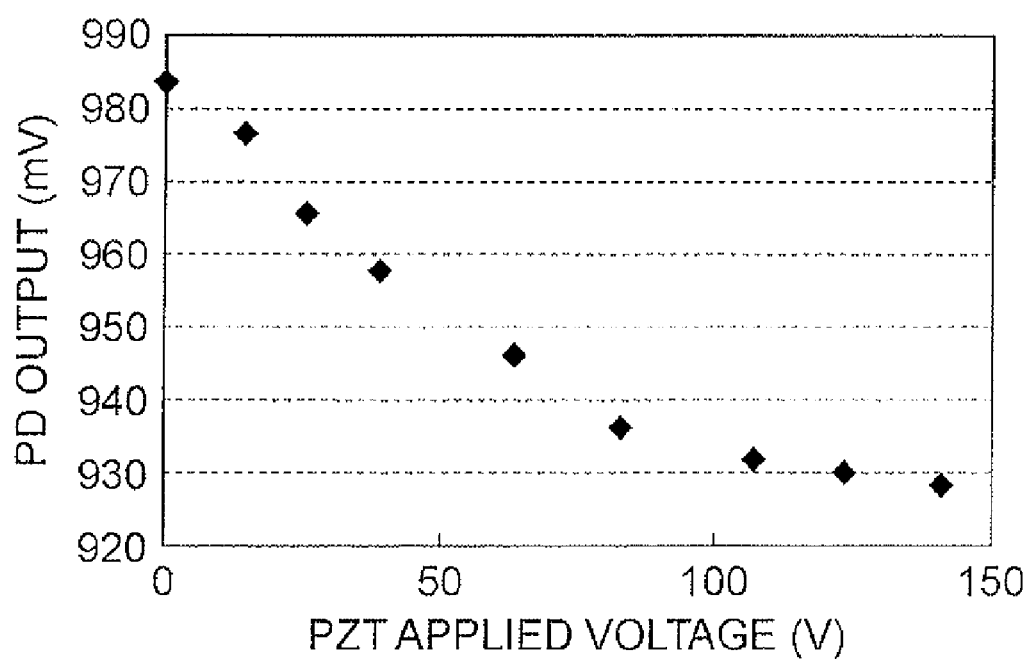
FIG. 3 is a view showing characteristics of the optical path length difference adjustment unit 50A.

Here, if it is assumed that moving distance of the mirror 101 by the piezoelectric element 103 is $\delta d$ and an angle of incidence of the light to the mirror 101 is $\theta$, the light finally reflected by the mirror 102 and input into the collimator 105 is moved by the distance of $(2\delta d \cdot \sin \theta)$ in a direction perpendicular to the incidence direction to the collimator 105. Therefore, as shown in FIG. 3, if the applied voltage to the piezoelectric element 103 becomes large and moving distance $\delta d$ of the mirror 101 becomes large, intensity of the light coupled to the collimator 105 becomes smaller. Although the intensity of the light thus changes, it has no effect on detection of phase difference $\phi$.

Figure 4:
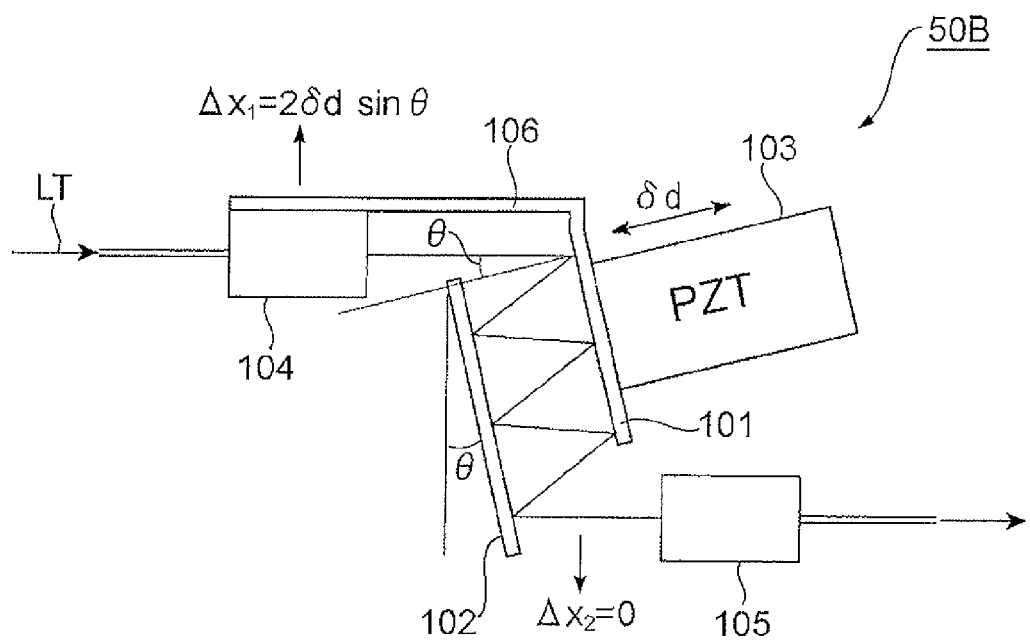
FIG. 4 is a view showing a configuration of an optical path length difference adjustment unit 50B as an example of the optical path length difference adjustment unit 50.

FIG. 4 is a view showing a configuration of an optical path length difference adjustment unit 50B as an example of the optical path length difference adjustment unit 50. Similar to the optical path length difference adjustment unit 50A, the optical path length difference adjustment unit 50B shown in this figure includes the mirror 101, the mirror 102, the piezoelectric element 103, the collimator 104, and the collimator 105, and in addition a mechanism 106 for enabling change in position of the collimator 104. Thus, the collimator 104 is moved by the distance $(2\delta d \cdot \sin \theta)$ in accordance with the moving distance $\delta d$ of the mirror 101 by the piezoelectric element 103, so that intensity of the light coupled to the collimator 105 can be maintained constant.

Figure 5:
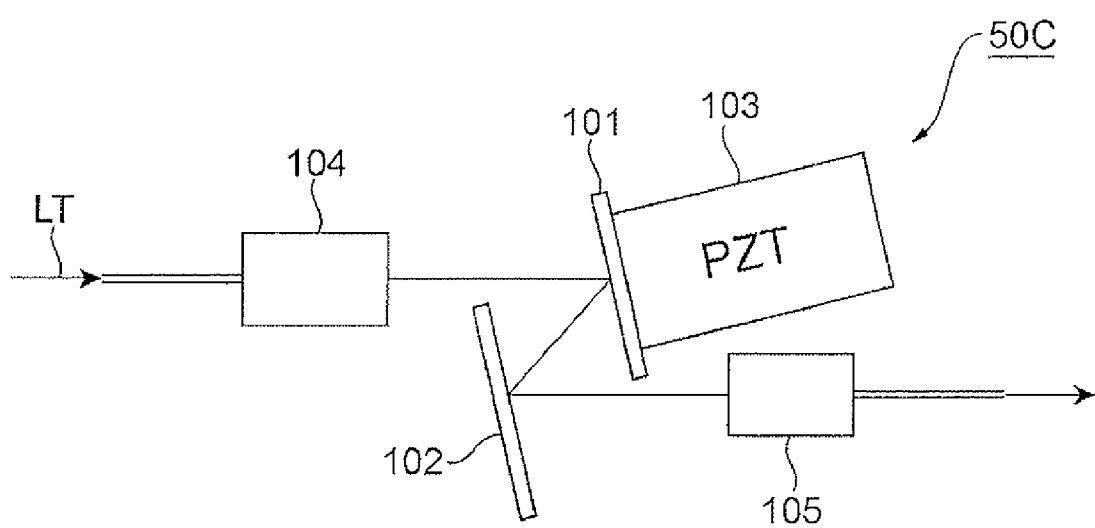
FIG. 5 is a view showing a configuration of an optical path length difference adjustment unit 50C as an example of the optical path length difference adjustment unit 50.

FIG. 5 is a view showing a configuration of an optical path length difference adjustment unit 50C as an example of the optical path length difference adjustment unit 50. Similar to the optical path length difference adjustment unit 50A, the optical path length difference adjustment unit 50C shown in this figure includes the mirror 101, the mirror 102, the piezoelectric element 103, the collimator 104, and the collimator 105, however, reflection by the mirror 101 and the mirror 102 is carried out only twice (once for one mirror).

Figure 6:
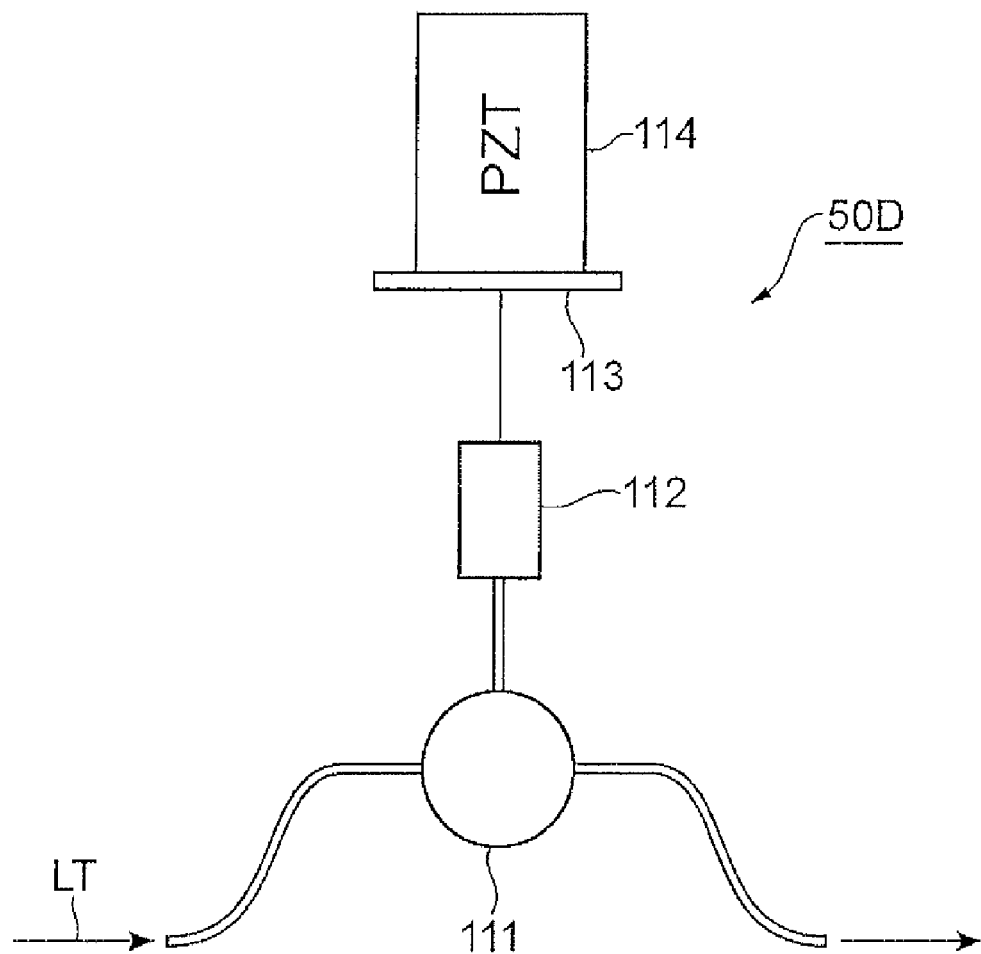
FIG. 6 is a view showing a configuration of an optical path length difference adjustment unit 50D as an example of the optical path length difference adjustment unit 50.

FIG. 6 is a view showing a configuration of an optical path length difference adjustment unit 50D as an example of the optical path length difference adjustment unit 50. The optical path length difference adjustment unit 50D shown in this figure includes an optical circulator 111, a collimator 112, a piezoelectric element 114, and a mirror 113. The optical circulator 111 inputs the light LT reached from the phase modulation unit 40 and outputs the light to the collimator 112, and inputs light reached from the collimator 112 and outputs the light to the second optical coupler 22. The collimator 112 collimates the light reached from the optical circulator 111 to output the light to the mirror 113, and also inputs light reflected and reached from the mirror 113. The mirror 113 is moved by the piezoelectric element 114 in a direction perpendicular to the reflection surface. The mirror 113 is moved by the piezoelectric element 114 in this optical path length difference adjustment unit 50D to change the interval between the mirror 113 and the collimator 112, so that the optical path length between an input end and an output end of the optical circulator 111 is changed.

Figure 7:
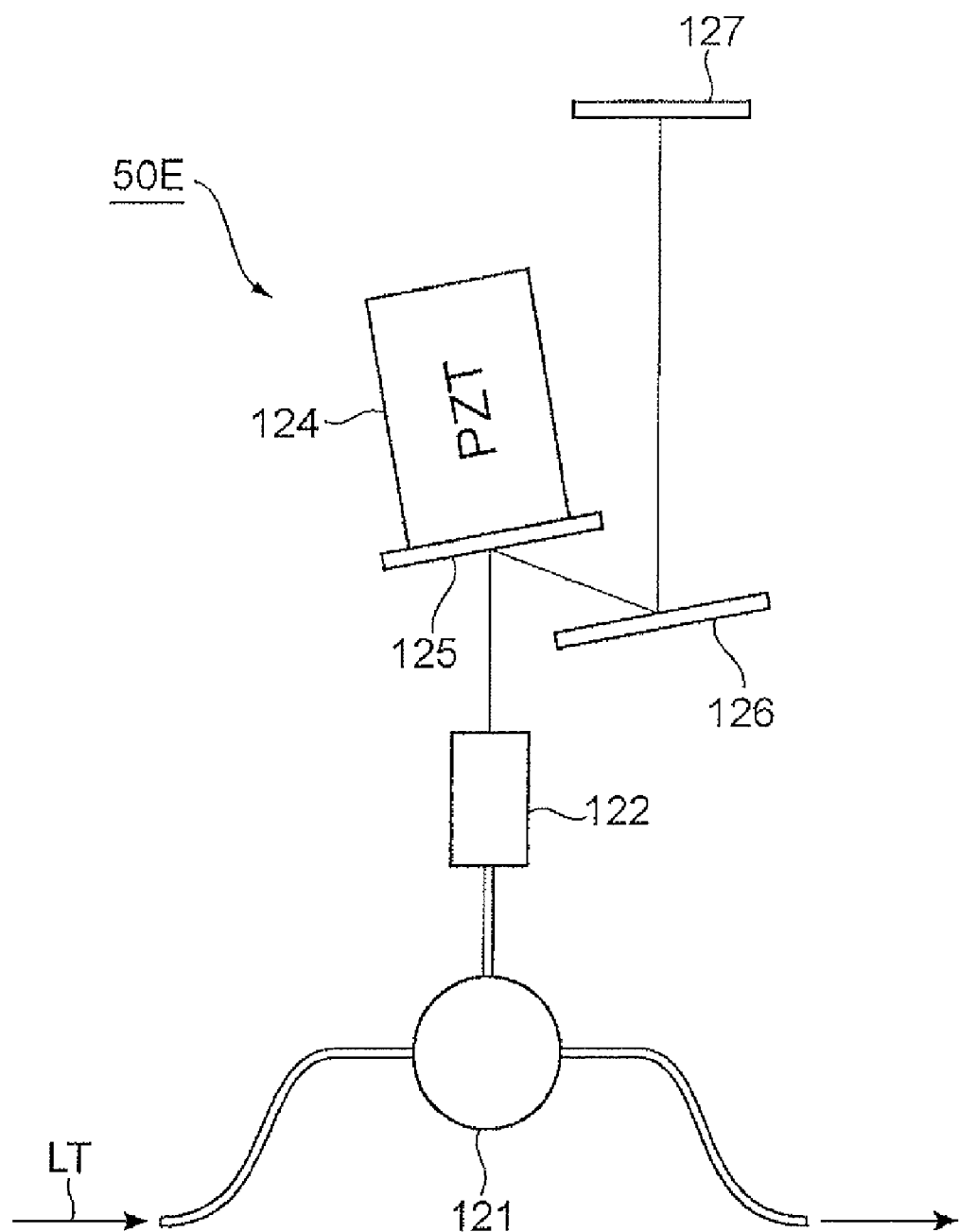
FIG. 7 is a view showing a configuration of an optical path length difference adjustment unit 50E as an example of the optical path length difference adjustment unit 50.

FIG. 7 is a view showing a configuration of an optical path length difference adjustment unit 50E as an example of the optical path length difference adjustment unit 50. The optical path length difference adjustment unit 50E shown in this figure includes an optical circulator 121, a collimator 122, a piezoelectric element 124, and mirrors 125 to 127. The optical circulator 121 inputs the light LT reached from the phase modulation unit 40 and outputs the light to the collimator 122, and inputs light reached from the collimator 122 and outputs the light to the second optical coupler 22. The collimator 122 collimates the light reached from the optical circulator 121 to output the light to the mirror 125, and also inputs light reflected and reached from the mirror 125. The mirror 125 reflects the light reached from the collimator 122 to the mirror 126 and reflects the light reached from the mirror 126 to the collimator 122, and the mirror is also moved by the piezoelectric element 124 in a direction perpendicular to the reflection surface. The mirror 126 causes the light reached from the mirror 125 to be incident and transmits the light to the mirror 127 and outputs the light reached from the mirror 127 to the mirror 125. The mirror 125 is moved by the piezoelectric element 124 in this optical path length difference adjustment unit 50E to change the interval between the mirror 127 and the collimator 122, so that the optical path length between an input end and an output end of the optical circulator 121 is changed.

Figure 8:
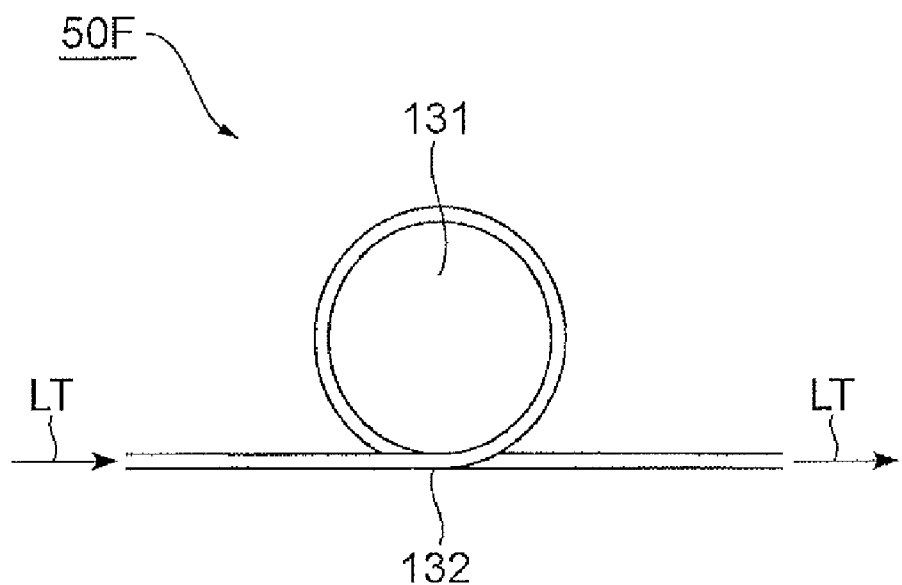
FIG. 8 is a view showing a configuration of an optical path length difference adjustment unit 50F as an example of the optical path length difference adjustment unit 50.

FIG. 8 is a view showing a configuration of an optical path length difference adjustment unit 50F as an example of the optical path length difference adjustment unit 50. The optical path length difference adjustment unit 50F shown in this figure includes a cylindrical piezoelectric vibrator 131 around which an optical fiber 132 is twisted and enables to change the optical path length of the optical fiber 132 by extension and contraction of the diameter of the cylindrical piezoelectric vibrator 131.

Next, operation of the optical property measurement apparatus 1 according to the first embodiment will be explained. Light emitted from the light source unit 10 is branched into two by the first optical coupler 21 and output as the first branched light and the second branched light. The first branched light output to the first branched light path P1 from the first optical coupler 21 is phase modulated sinusoidally by the phase modulation unit 40 driven by the drive unit 41 with the frequency f and is input into the second optical coupler 22 through the optical path length difference adjustment unit 50 controlled by the control unit 51. The second branched light output to the second branched light path P2 from the first optical coupler 21 is collimated or converged by the lens 31 and output, and the light thus output is input into the lens 32 after passing through the flow passage 90 and is input into the second optical coupler 22.

The first branched light and the second branched light input into the second optical coupler 22 interfere with each other in the second optical coupler 22, and interfering light is output from the second coupler 22. The interfering light output from the second coupler 22 is received by the light receiving unit 60 and an electrical signal having a value corresponding to the intensity of the received light is output from the light receiving unit 60. The electrical signal output from the light receiving unit 60 is input into the synchronization detection unit 70, and at the same time, a modulation signal of the frequency f and a modulation signal of the frequency 2f are input from the drive unit 41. Then, the first signal having a value corresponding to the magnitude of the component of the frequency f included in the electrical signal output from the light receiving unit 60 is output from the synchronization detection unit 70, and at the same time, the second signal having a value corresponding to the magnitude of the component of the frequency f2 included in the electrical signal is output.

The first signal and the second signal output from the synchronization detection unit 70 are input into the measurement unit 80 and an optical property of a sample in the flow passage 90 is measured on the basis of the first signal and the second signal. Moreover, the optical path length difference adjusted by the optical path length difference adjustment unit 50 is controlled to be a predetermined value by the control unit 51 on the basis of the first signal or the second signal output from the synchronization detection unit 70.

Here, it is assumed that a wavelength of the light output from the light source unit 10 is $\lambda$. Moreover, it is assumed that difference L in the optical path lengths of the first branched light path P1 and the second branched light path P2 provided between the first optical coupler 21 and the second optical coupler 22 is, as expressed by the following equation (1), set to be a center value $L_0$ by the optical path length difference adjustment unit 50, and at the same time, is minutely fluctuated in a sinusoidal manner with the amplitude $\Delta L$ and the frequency f in the vicinity of the center value $L_0$ by the phase modulation unit 40. Here, t is a time variable.

$$L = L_0 + \Delta L \cdot \sin(2\pi f t) \quad (1)$$

At this time, intensity I(t) of the interfering light received by the light receiving unit 60 is expressed by the following equation (2). If approximation is carried out using the fact that the $\Delta \phi$ is sufficiently smaller than $2\pi$, the equation (2) mainly includes a component of the frequency f and a component of the frequency 2f. Among them, the component of the frequency f is expressed by a formula of $A\sin \phi$ and the component of the frequency 2f is expressed by a formula of $A\cos \phi$. Here, A is a constant number. Therefore, the ratio of the two components is expressed by $\tan \phi$ (or $\cot \phi$, an inverse thereof).

$$I(t) = 1 + \cos \{\phi + \Delta\phi \cdot \sin(2\pi f t)\}$$

$$\phi = 2\pi \cdot L_0 / \lambda,$$

$$\Delta\phi = 2\pi \cdot \Delta L / \lambda \quad (2)$$

That is, since the first signal output from the synchronization detection unit 70 has a value corresponding to the magnitude of the component of the frequency f included in the electrical signal output from the light receiving unit 60, the first signal is expressed by the formula of $A\sin \phi$. Moreover, since the second signal output from the synchronization detection unit 70 has a value corresponding to the magnitude of the component of the frequency 2f included in the electrical signal output from the light receiving unit 60, the second signal is expressed by the formula of $A\cos \phi$. Further, $\tan \phi$ or $\cot \phi$ which is the ratio of values of the first signal ($A\sin \phi$) and the second signal ($A\cos \phi$) respectively is acquired in the measurement unit 80, and on the basis of the value of $\tan \phi$ or $\cot \phi$, phase difference $\phi$ between the first branched light path P1 and the second branched light path P2 (i.e., optical path length difference $L_0$) is obtained. Then, on the basis of the phase difference $\phi$, phase difference of the sample is measured in the flow passage 90.

In a case where the phase difference $\phi$ is obtained on the basis of the value of $\tan \phi$ in the measurement unit 80, if the value of the second signal ($A\cos \phi$) is 0 (or nearly 0), that is, the phase difference $\phi$ is $\pi/2$ or $3\pi/2$ (optical path length difference $L_0$ is $\lambda/4$ or $3\lambda/4$), measurement sensitivity is maximized. Therefore, in this case, the optical path length difference adjusted by the optical path length difference adjustment unit 50 is controlled by the control unit 51 so that the absolute value of the second signal ($A\cos \phi$) output from the synchronization detection unit 70 becomes small.

Figure 9:
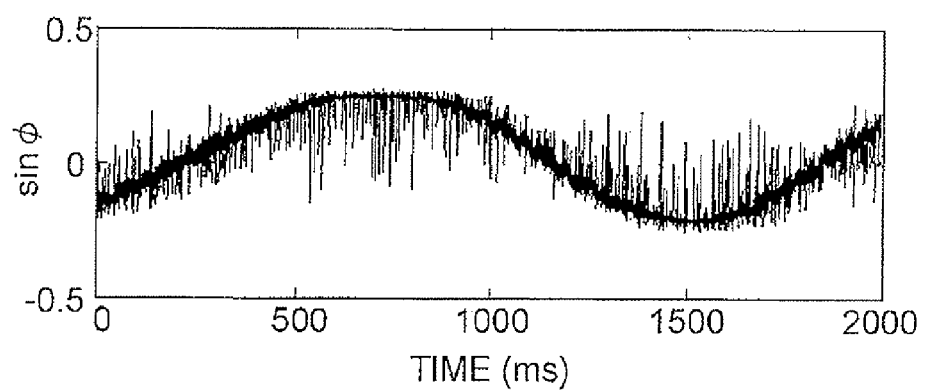
FIG. 9 is a view showing a first signal (A sin ϕ) and a second signal (A cos ϕ) output from a synchronization detection unit 70 in a case where control of optical path length difference is not carried out.
Figure 9:
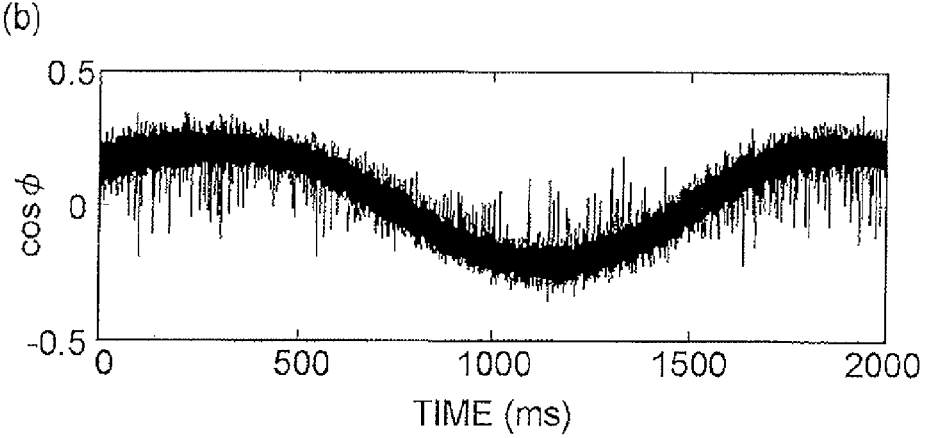
Figure 10:
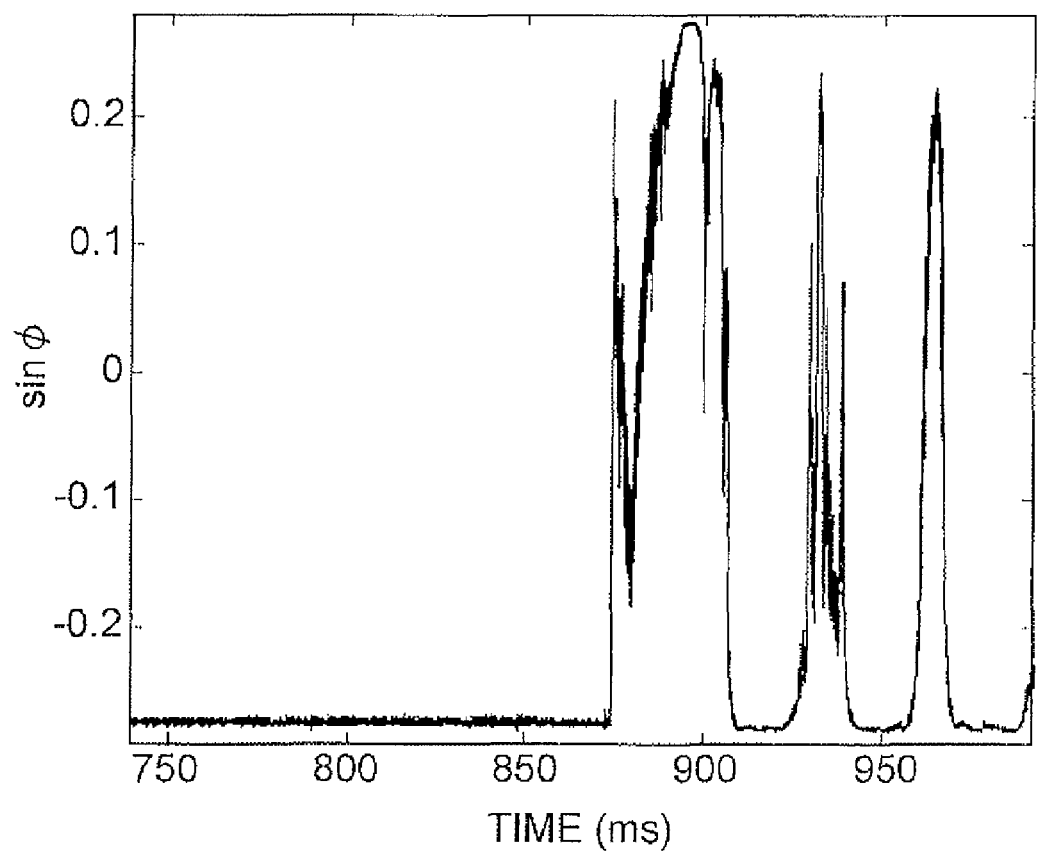
FIG. 10 is a view showing the first signal (A sin ϕ) output from the synchronization detection unit 70 in a case where control of optical path length difference is carried out and in a case where control of optical path length difference is not carried out, respectively.

FIG. 9 and FIG. 10 are views respectively showing the first signal ($A\sin \phi$) and the second signal ($A\cos \phi$) output from the synchronization detection unit 70 included in the optical property measurement apparatus 1 according to the first embodiment In a case where the optical path length difference is not controlled by the control unit 51 and the optical path length difference adjustment unit 50, due to a change in environment such as temperature, the first signal ($A\sin \phi$) and the second signal ($A\cos \phi$) output from the synchronization detection unit 70 fluctuate with an approximate cycle of 0.1 to 0.5 Hz, as shown in FIG. 9 and FIG. 10 (in the latter part). On the contrary, in a case where the optical path length difference is controlled by the control unit 51 and the optical path length difference adjustment unit 50, the first signal ($A\sin \phi$) output from the synchronization detection unit 70 is stabilized, as shown in FIG. 10 (in the early part).

As described above, the optical property measurement apparatus 1 according to the first embodiment can control the optical path length difference to be a predetermined value even when a sample particle is not crossing the branched light and in a case where each of the sample particles is moving one by one in the flow passage, the optical property of the sample can be measured with constant sensitivity.

Second Embodiment

Figure 11:
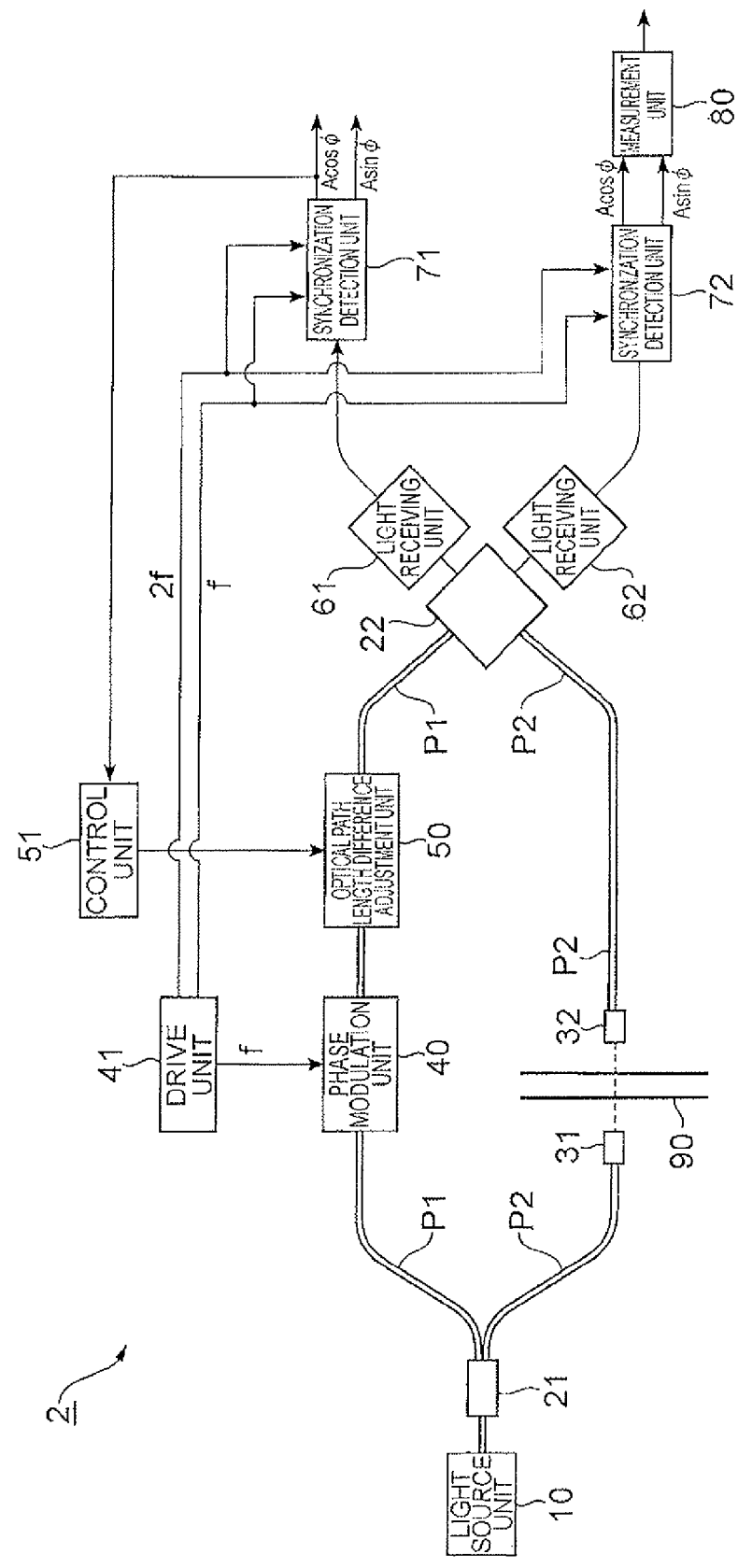
FIG. 11 is a view showing a configuration of an optical property measurement apparatus 2 according to a second embodiment.

Next, a second embodiment of an optical property measurement apparatus according to the present invention will be explained. FIG. 11 is a view showing a configuration of an optical property measurement apparatus 2 according to the second embodiment. Compared with the optical property measurement apparatus 1 according to the first embodiment shown in FIG. 1, the optical property measurement apparatus 2 according to the second embodiment shown in FIG. 11 differs from the optical property measurement apparatus 1 in the following points: a first light receiving unit 61 and a second light receiving unit 62 are provided instead of the light receiving unit 60, a first synchronization detection unit 71 and a second synchronization detection unit 72 are provided instead of the synchronization detection unit 70, the control unit 51 carries out control on the basis of a signal output from the first synchronization detection unit 71, and the measurement unit 80 carries out measurement on the basis of a signal output from the second synchronization detection unit 72.

The first light receiving unit 61 selectively receives zero-order light in the interfering light output from the second optical coupler 22 and outputs a first electrical signal having a value corresponding to the received light intensity to the synchronization detection unit 71. The second light receiving unit 62 selectively receives high-order light in the interfering light output from the second optical coupler 22 and outputs a second electrical signal having a value corresponding to the received light intensity to the synchronization detection unit 72. Each of the first light receiving unit 61 and the second light receiving unit 62 includes, for example, a photodiode.

The first synchronization detection unit 71 inputs the first electrical signal output from the first light receiving unit 61, and outputs a first signal (Asin φ) having a value corresponding to the magnitude of the component of the frequency f included in the first electrical signal, or a second signal (Acos φ) having a value corresponding to the magnitude of the component of the frequency 2f included in the first electrical signal. The second synchronization detection unit 72 inputs the second electrical signal output from the second light receiving unit 62, outputs a third signal (Asin φ) having a value corresponding to the magnitude of the component of the frequency f included in the second electrical signal, and also outputs a fourth signal (Acos φ) having a value corresponding to the magnitude of the component of the frequency 2f included in the second electrical signal. Each of the first synchronization detection unit 71 and the second synchronization detection unit 72 includes, for example, a lock-in amplifier.

The control unit 51 controls the optical path length difference, adjusted by the optical path length difference adjustment unit 50, to be a predetermined value on the basis of the first signal (Asin φ) or the second signal (Acos φ) output from the first synchronization detection unit 71. The control carried out by the control unit 51 is similar to that in the case of the first embodiment. The measurement unit 80 measures an optical property of a sample in the flow passage 90 on the basis of the third signal (Asin φ) and the fourth signal (Acos φ) output from the second synchronization detection unit 72. The processing carried out by the measurement unit 80 is similar to that in the case of the first embodiment.

Next, configuration examples of the second optical coupler 22, the first light receiving unit 61, and the second light receiving unit 62 included in the optical property measurement apparatus 2 according to the second embodiment will be explained using FIG. 12 to FIG. 14.

Figure 12:
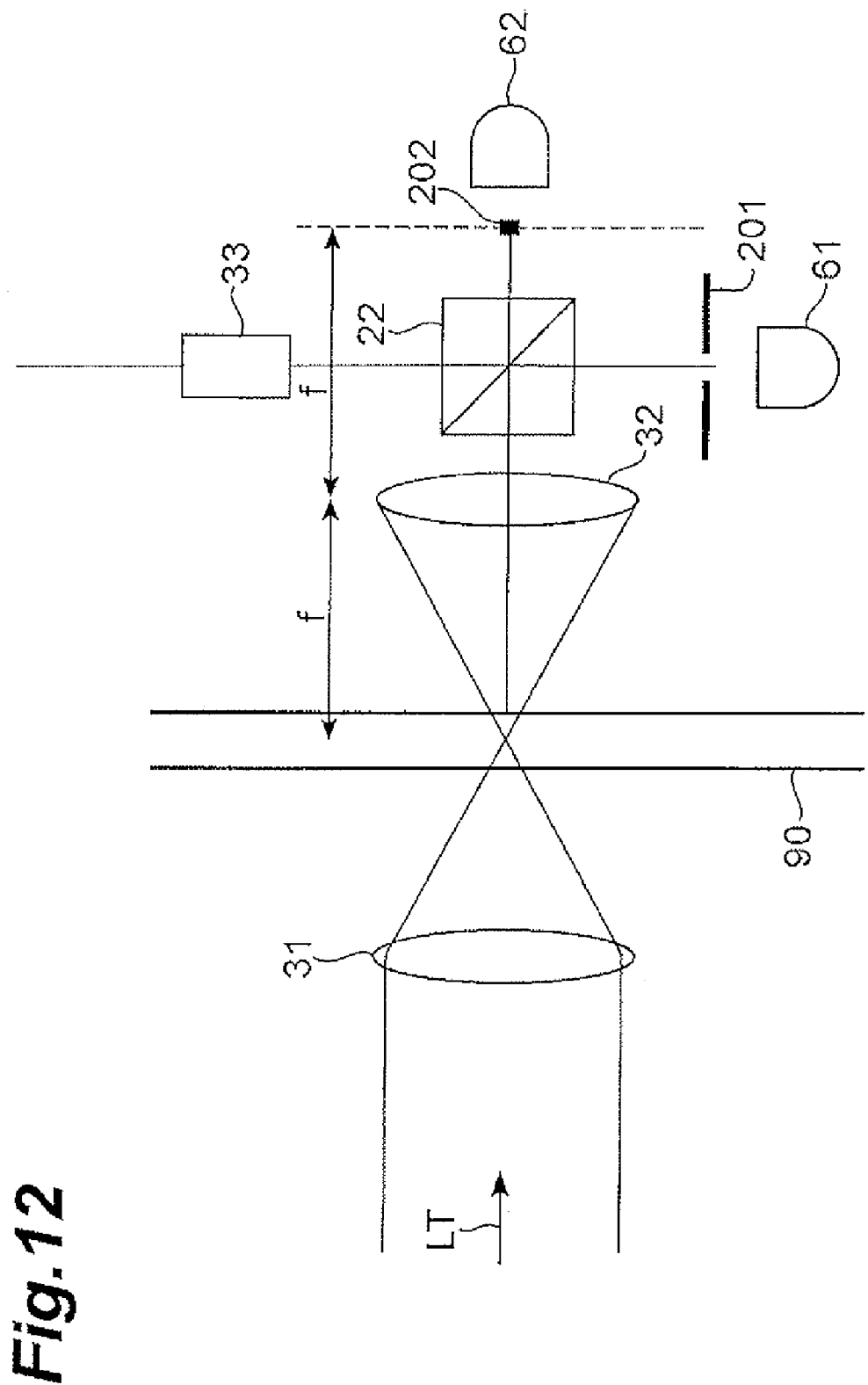
FIG. 12 is a view showing a configuration example of a first light receiving unit 61 and a second light receiving unit 62.

In the configuration example shown in FIG. 12, the flow passage 90 is provided at a posterior focal position of the lens 31 and at an anterior focal position of the lens 32. The second optical coupler 22 is a beam splitter, which inputs the first branched light which passed through the first branched light path P1 and is collimated and output by the collimator 33, inputs the second branched light converged and output by the lens 32, causes the first branched light and the second branched light to interfere with each other, and outputs interfering light to the first light receiving unit 61 and the second light receiving unit 62.

A pinhole 201 provided between the second optical coupler 22 and the first light receiving unit 61 is at a posterior focal position of the lens 32, and causes zero-order light of the interfering light reached from the second optical coupler 22 to pass through, while blocking high-order light of the interfering light reached from the second optical coupler 22. The first light receiving unit 61 receives the zero-order light which passed through the pinhole 201. A stopper 202 provided between the second optical coupler 22 and the second light receiving unit 62 is at a posterior focal position of the lens 32, and blocks the zero-order light of the interfering light reached from the second optical coupler 22, while causing the high-order light of the interfering light reached from the second optical coupler 22 to pass through. The second light receiving unit 62 receives the high-order light which passed through the stopper 202.

Figure 13:
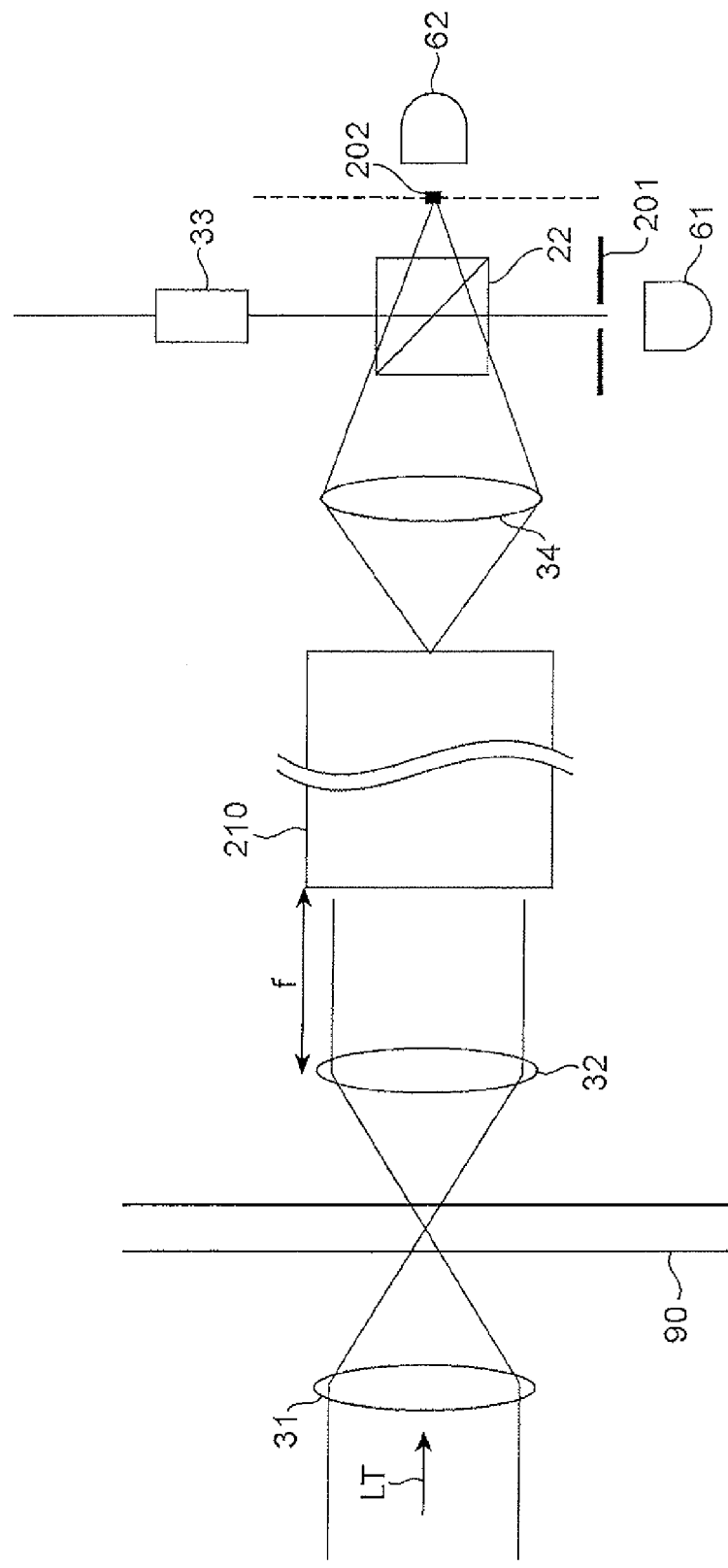
FIG. 13 is a view showing a configuration example of the first light receiving unit 61 and the second light receiving unit 62.

In the configuration example shown in FIG. 13, the flow passage 90 is provided at a posterior focal position of the lens 31 and at an anterior focal position of the lens 32. The second optical coupler 22 is a beam splitter, which inputs the first branched light which passed through the first branched light path P1 and is collimated and output by the collimator 33, and an image is collimated by the lens 32, guided by a multicore optical fiber 210 having an input end face at the posterior focal position of the lens 32, and the image on an output end face of the multicore fiber 210 is formed on the pinhole 201 and the stopper 202 by a relay lens 34. The second optical coupler 22 also inputs the second branched light which passed through all of the above and output, and causes the first branched light and the second branched light to interfere with each other to output the interfering light to the first light receiving unit 61 and the second light receiving unit 62.

The pinhole 201 provided between the second optical coupler 22 and the first light receiving unit 61 is at an image plane position where an image is formed by the relay lens 34, causes the zero-order light of the interfering light reached from the second optical coupler 22 to pass through, and blocks the high-order light of the interfering light reached from the second optical coupler 22. The first light receiving unit 61 receives the zero-order light which passed through the pinhole 201. The stopper 202 provided between the second optical coupler 22 and the second light receiving unit 62 is at an image plane position where an image is formed by the relay lens 34, blocks the zero-order light of the interfering light reached from the second optical coupler 22, and causes the high-order light of the interfering light reached from the second optical coupler 22 to pass through. The second light receiving unit 62 receives the high-order light which passed through the stopper 202.

Figure 14:
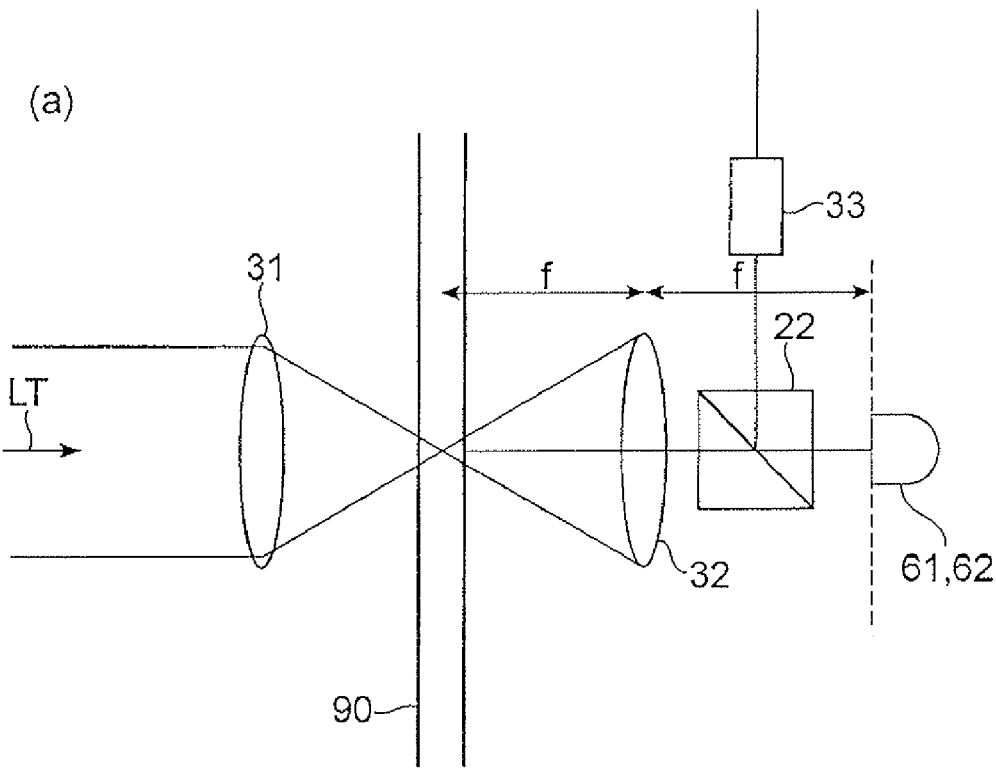
FIG. 14 is a view showing a configuration example of the first light receiving unit 61 and the second light receiving unit 62.
Figure 14:
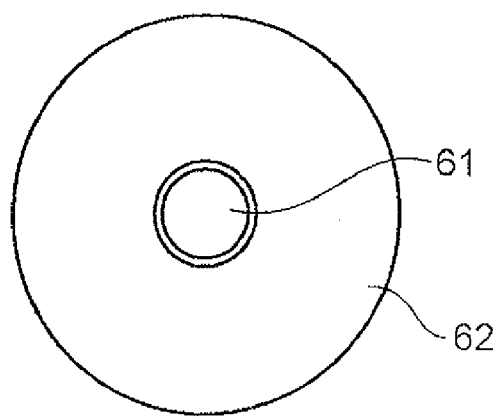

In the configuration example shown in FIG. 14, the flow passage 90 is provided at a posterior focal position of the lens 31 and at an anterior focal position of the lens 32. The second optical coupler 22 is a beam splitter, which inputs the first branched light collimated and output by the collimator 33 through the first branched light path P1, also inputs the second branched light collimated and output by the lens 32, and causes the first branched light and the second branched light to interfere with each other so that interfering light is output to the first light receiving unit 61 and the second light receiving unit 62.

The first light receiving unit 61 and the second light receiving unit 62 are at a posterior focal position of the lens 32 as shown in (b) in the figure, and include one element having two light receiving regions. That is, a light receiving region in the center portion is for selectively receiving the zero-order light of the interfering light reached from the second optical coupler 22, and functions as the first light receiving unit 61. An annular light receiving region in the circumference thereof is for selectively receiving the high-order light of the interfering light reached from the second optical coupler 22, and functions as the second light receiving unit 62.

Next, operation of the optical property measurement apparatus 2 according to the second embodiment will be explained. Light emitted from the light source unit 10 is branched into two by the first optical coupler 21 and output as the first branched light and the second branched light. The first branched light output to the first branched light path P1 from the first optical coupler 21 is phase modulated to be sinusoidal by the phase modulation unit 40 driven by the drive unit 41 with the frequency f and is input into the second optical coupler 22 through the optical path length difference adjustment unit 50 controlled by the control unit 51. The second branched light output to the second branched light path P2 from the first optical coupler 21 is collimated or converged by the lens 31 and output, and the light thus output is input into the lens 32 after passing through the flow passage 90 and is input into the second optical coupler 22.

The first branched light and the second branched light input into the second optical coupler 22 interfere with each other in the second optical coupler 22, and interfering light is output from the second coupler 22. The zero-order light in the interfering light output from the second optical coupler 22 is selectively received by the first light receiving unit 61 and a first electrical signal having a value corresponding to the intensity of the received light is output from the first light receiving unit 61 to the synchronization detection unit 71. The high-order light in the interfering light output from the second optical coupler 22 is selectively received by the second light receiving unit 62 and a second electrical signal having a value corresponding to the intensity of the received light is output from the second light receiving unit 62 to the synchronization detection unit 72.

The first electrical signal output from the first light receiving unit 61 is input to the first synchronization detection unit 71, and at the same time, a modulation signal of the frequency f and a modulation signal of the frequency 2f are input from the drive unit 41. A first signal (Asin φ) having a value corresponding to the magnitude of the component of the frequency f included in the first electrical signal output from the first light receiving unit 61 is output from the first synchronization detection unit 71, and at the same time, a second signal (Acos φ) having a value corresponding to the magnitude of the component of the frequency 2f included in the first electrical signal is output. Then, on the basis of the first signal (Asin φ) or the second signal (Acos φ) output from the first synchronization detection unit 71, the optical path length difference adjusted by the optical path length difference adjustment unit 50 is controlled to be a predetermined value by the control unit 51. The control carried out by the control unit 51 is similar to that in the first embodiment.

The second electrical signal output from the second light receiving unit 62 is input to the second synchronization detection unit 72, and at the same time, a modulation signal of the frequency f and a modulation signal of the frequency 2f are input from the drive unit 41. A third signal (Asin φ) having a value corresponding to the magnitude of the component of the frequency f included in the second electrical signal output from the second light receiving unit 62 is output from the second synchronization detection unit 72, and at the same time, a fourth signal (Acos φ) having a value corresponding to the magnitude of the component of the frequency 2f included in the second electrical signal is output. Then, on the basis of the third signal (Asin φ) and the fourth signal (Acos φ) output from the second synchronization detection unit 72, an optical property of a sample in the flow passage 90 is measured by the measurement unit 80. The processing carried out by the measurement unit 80 is similar to that in the first embodiment.

As described above, the optical property measurement apparatus 2 according to the second embodiment can also control the optical path length difference to be a predetermined value even when a sample particle is not crossing the branched light and in a case where sample particles are moving one by one in the flow passage, the optical property of the sample can be measured with constant sensitivity.

Especially, in the optical property measurement apparatus 2 according to the second embodiment, the optical path length difference adjusted by the optical path length difference adjustment unit 50 is controlled to be a predetermined value on the basis of the first signal (Asin φ) or the second signal (Acos φ) obtained from the zero-order light of the interfering light output from the second optical coupler 22 by the first light receiving unit 61 and the first synchronization detection unit 71. Moreover, the optical property of the sample in the flow passage 90 is measured by the measurement unit 80 on the basis of the third signal (Asin φ) and the fourth signal (Acos φ) obtained from the high-order light of the interfering light output from the second optical coupler 22 by the second light receiving unit 62 and the second synchronization detection unit 72. Therefore, measurement sensitivity is high even in a case where intensity of the high-order light is weak when compared to the zero-order light.

The invention claimed is:

1. An optical property measurement apparatus for measuring an optical property of a sample in a flow passage using optical interference comprising:
    a light source unit for emitting light;
    a first optical coupler for branching the light emitted from the light source unit into two light components and outputting the light components as first branched light and second branched light;
    a second optical coupler for inputting the first branched light output from the first optical coupler and passed through a first branched light path, inputting the second branched light output from the first optical coupler and passed through a second branched light path and a flow passage on the second branched light path, and causing the first branched light and the second branched light thus input to interfere with each other to output interfering light;
    a phase modulation unit provided on the first branched light path or the second branched light path between the first optical coupler and the second optical coupler for carrying out phase modulation of the light, which is propagated on the light path, with a frequency f;
    an optical path length difference adjustment unit for adjusting a difference in the respective optical path lengths of the first branched light path and the second branched light path between the first optical coupler and the second optical coupler;
    a light receiving unit for receiving the interfering light output from the second optical coupler and outputting an electrical signal having a value corresponding to the received light intensity;
    a synchronization detection unit for inputting the electrical signal output from the light receiving unit, outputting a first signal having a value which corresponds to a magnitude of a component of the frequency f included in the electrical signal, and outputting a second signal having a value which corresponds to a magnitude of a component of a frequency 2f included in the electrical signal;
    a control unit for controlling the optical path length difference adjusted by the optical path length difference adjustment unit to be a predetermined value based on the first signal or the second signal output from the synchronization detection unit; and
    a measurement unit for measuring an optical property of a sample in the flow passage based on the first signal and the second signal output from the synchronization detection unit,
    wherein control by the control unit is carried out via a low-pass filter which transmits a variation frequency of the optical path length difference caused by change in environment and blocks a frequency including a signal generated when the sample passes through.

2. An optical property measurement apparatus for measuring an optical property of a sample in a flow passage using optical interference comprising:

a light source unit for emitting light;

a first optical coupler for branching the light emitted from the light source unit into two light components and outputting the light components as first branched light and second branched light;

a second optical coupler for inputting the first branched light output from the first optical coupler and passed through a first branched light path, inputting the second branched light output from the first optical coupler and passed through a second branched light path and a flow passage on the second branched light path, and causing the first branched light and the second branched light thus input to interfere with each other to output interfering light;

a phase modulation unit provided on the first branched light path or the second branched light path between the first optical coupler and the second optical coupler for carrying out phase modulation of the light, which is propagated on the light path, with a frequency f;

an optical path length difference adjustment unit for adjusting a difference in the respective optical path lengths of the first branched light path and the second branched light path between the first optical coupler and the second optical coupler;

a first light receiving unit for selectively receiving zero-order light in the interfering light output from the second optical coupler and outputting a first electrical signal having a value corresponding to the received light intensity;

a second light receiving unit for selectively receiving high-order light in the interfering light output from the second optical coupler and outputting a second electrical signal having a value corresponding to the received light intensity;

a first synchronization detection unit for inputting the first electrical signal output from the first light receiving unit, and outputting a first signal having a value which corresponds to a magnitude of a component of the frequency f included in the first electrical signal, or a second signal having a value which corresponds to a magnitude of a component of a frequency $2f$ included in the first electrical signal;

a second synchronization detection unit for inputting the second electrical signal output from the second light receiving unit, outputting a third signal having a value which corresponds to a magnitude of a component of the frequency f included in the second electrical signal, and outputting a fourth signal having a value which corresponds to a magnitude of a component of the frequency 2f included in the second electrical signal;

a control unit for controlling the optical path length difference adjusted by the optical path length difference adjustment unit to be a predetermined value based on the first signal or the second signal output from the first synchronization detection unit; and a measurement unit for measuring an optical property of a sample in the flow passage based on the third signal and the fourth signal output from the second synchronization detection unit.

* * * * *